(12) United States Patent
Salys

(10) Patent No.: US 11,235,137 B2
(45) Date of Patent: Feb. 1, 2022

(54) MINIMALLY INVASIVE METHODS AND DEVICES FOR VENTRICULAR ASSIST DEVICE IMPLANTATION

(71) Applicant: TC1 LLC, St. Paul, MN (US)

(72) Inventor: Scott Salys, Dublin, CA (US)

(73) Assignee: TC1 LLC, St. Paul, MN (US)

( * ) Notice: Subject to any disclaimer, the term of this patent is extended or adjusted under 35 U.S.C. 154(b) by 156 days.

(21) Appl. No.: 15/903,394

(22) Filed: Feb. 23, 2018

(65) Prior Publication Data

US 2018/0243492 A1 Aug. 30, 2018

Related U.S. Application Data

(60) Provisional application No. 62/463,337, filed on Feb. 24, 2017.

(51) Int. Cl.
*A61M 60/00* (2021.01)
*A61M 60/148* (2021.01)
(Continued)

(52) U.S. Cl.
CPC .......... *A61M 60/148* (2021.01); *A61M 60/50* (2021.01); *A61M 60/857* (2021.01);
(Continued)

(58) Field of Classification Search
CPC .... A61M 1/122; A61M 1/1008; A61M 1/125; A61B 2017/00243
See application file for complete search history.

(56) References Cited

U.S. PATENT DOCUMENTS 3,766,567 A 10/1973 Kahn et al.
4,099,759 A 7/1978 Kornhauser
(Continued)

FOREIGN PATENT DOCUMENTS

CA 2526920 2/2009
CN 1842354 A 10/2006
(Continued)

OTHER PUBLICATIONS

Barletta et al., "Design of a bearing less blood pump", Proc.3rd Int. Symp. on Magnetic Suspension Technology, Dec. 13-15, 1995, pp. 265-274.
(Continued)

*Primary Examiner* — Eric D. Bertram
(74) *Attorney, Agent, or Firm* — Kilpatrick Townsend & Stockton LLP

(57) ABSTRACT

Methods and devices for implanting a ventricular assist device employ a coupler that engages an aperture formed in a heart wall and provides a conduit by which blood is pumped from the ventricle via the ventricular assist device. A method includes penetrating a distal end of a delivery device through a wall of a heart into a ventricle of the heart to form an aperture having a diameter in the wall. A coupler is deployed from the delivery device so that the coupler engages the aperture, expands the diameter of the aperture, and forms a conduit for a flow of blood from the ventricle. The delivery device is removed from the ventricle by retracting the delivery device through the conduit. The ventricular assist device is coupled to the coupler to receive the flow of blood from the ventricle and pump the flow of blood to assist circulation in the patient.

15 Claims, 9 Drawing Sheets

(51) Int. Cl.
    *A61M 60/50*      (2021.01)
    *A61M 60/857*     (2021.01)
    *A61B 17/00*          (2006.01)
    *A61F 2/24*           (2006.01)
    *A61M 60/135*         (2021.01)

(52) U.S. Cl.
    CPC .............. *A61B 2017/00243* (2013.01); *A61F 2002/2484* (2013.01); *A61M 60/135* (2021.01)

(56) References Cited

U.S. PATENT DOCUMENTS

| | | | |
|---|---|---|---|
| 4,458,366 A | 7/1984 | MacGregor | |
| 4,688,998 A | 8/1987 | Olsen et al. | |
| 4,769,031 A | 9/1988 | McGough et al. | |
| 5,055,005 A | 10/1991 | Kletschka | |
| 5,098,369 A | 3/1992 | Heilman et al. | |
| 5,139,517 A | 8/1992 | Corral | |
| 5,195,877 A | 3/1993 | Kletschka | |
| 5,222,980 A | 6/1993 | Gealow | |
| 5,275,580 A | 1/1994 | Yamazaki | |
| 5,456,714 A | 10/1995 | Owen | |
| 5,470,208 A | 11/1995 | Kletschka | |
| 5,613,935 A | 3/1997 | Jarvik | |
| 5,708,346 A | 1/1998 | Schob | |
| 5,725,552 A | 5/1998 | Kotula et al. | |
| 5,814,005 A | 9/1998 | Barra et al. | |
| 5,827,316 A | 10/1998 | Young et al. | |
| 5,843,088 A | 12/1998 | Barra et al. | |
| 5,846,261 A | 12/1998 | Kotula et al. | |
| 5,944,738 A | 8/1999 | Amplatz et al. | |
| 5,984,956 A | 11/1999 | Tweden et al. | |
| 6,001,056 A | 12/1999 | Jassawalla et al. | |
| 6,050,975 A | 4/2000 | Poirier | |
| 6,066,085 A | 5/2000 | Heilman et al. | |
| 6,146,325 A | 11/2000 | Lewis et al. | |
| 6,168,622 B1 | 1/2001 | Mazzocchi | |
| 6,238,334 B1 | 5/2001 | Easterbrook, III et al. | |
| 6,254,564 B1 | 7/2001 | Wilk et al. | |
| 6,346,071 B1 | 2/2002 | Mussivand | |
| 6,390,976 B1 | 5/2002 | Spence et al. | |
| 6,447,531 B1 | 9/2002 | Amplatz | |
| 6,599,308 B2 | 7/2003 | Amplatz | |
| 6,669,708 B1 | 12/2003 | Nissenbaum et al. | |
| 6,673,043 B1 | 1/2004 | Landesberg | |
| 6,682,546 B2 | 1/2004 | Amplatz | |
| 6,689,147 B1 | 2/2004 | Koster, Jr. | |
| 6,705,988 B2 | 3/2004 | Spence et al. | |
| 6,726,648 B2 | 4/2004 | Kaplon et al. | |
| 6,732,501 B2 | 5/2004 | Yu et al. | |
| 6,802,806 B2 | 10/2004 | McCarthy et al. | |
| 6,808,498 B2 | 10/2004 | Laroya et al. | |
| 6,863,677 B2 | 3/2005 | Breznock | |
| 6,942,672 B2 | 9/2005 | Heilman et al. | |
| 6,994,666 B2 | 2/2006 | Shannon et al. | |
| 7,018,384 B2 | 3/2006 | Skakoon | |
| 7,048,681 B2 | 5/2006 | Tsubouchi et al. | |
| 7,056,286 B2 | 6/2006 | Ravenscroft et al. | |
| 7,077,801 B2 | 7/2006 | Haverich | |
| 7,214,234 B2 | 5/2007 | Rapacki et al. | |
| 7,303,553 B2 | 12/2007 | Ott | |
| 7,404,792 B2 | 7/2008 | Spence et al. | |
| 7,462,019 B1 | 12/2008 | Allarie et al. | |
| 7,824,358 B2 | 11/2010 | Cotter et al. | |
| 8,034,061 B2 | 10/2011 | Amplatz et al. | |
| 8,152,845 B2 | 4/2012 | Bourque | |
| 8,313,505 B2 | 11/2012 | Amplatz et al. | |
| 8,343,028 B2 | 1/2013 | Gregoric et al. | |
| 8,454,633 B2 | 6/2013 | Amplatz et al. | |
| 8,480,657 B2 | 7/2013 | Bakos et al. | |
| 8,500,759 B2 | 8/2013 | Koyfman et al. | |
| 8,579,790 B2 | 11/2013 | Jeffery et al. | |
| 8,870,739 B2 | 10/2014 | Larose et al. | |
| 8,882,697 B2 | 11/2014 | Celermajer et al. | |
| 8,951,223 B2 | 2/2015 | McNamara et al. | |
| 8,961,556 B2 | 2/2015 | Amplatz et al. | |
| 9,039,724 B2 | 5/2015 | Amplatz et al. | |
| 9,144,637 B2 | 9/2015 | Callaway et al. | |
| 9,199,019 B2 | 12/2015 | Callaway et al. | |
| 9,358,329 B2 | 6/2016 | Fitzgerald et al. | |
| 9,364,593 B2 | 6/2016 | McBride et al. | |
| 9,981,076 B2 | 5/2018 | Callaway et al. | |
| 9,981,077 B2 | 5/2018 | Callaway et al. | |
| 2002/0045846 A1 | 4/2002 | Kaplon et al. | |
| 2002/0095210 A1* | 7/2002 | Finnegan | A61F 2/064 623/3.26 |
| 2003/0023255 A1 | 1/2003 | Miles et al. | |
| 2003/0040765 A1 | 2/2003 | Breznock | |
| 2003/0130668 A1 | 7/2003 | Nieman et al. | |
| 2004/0002624 A1 | 1/2004 | Yu et al. | |
| 2004/0054251 A1 | 3/2004 | Liotta | |
| 2004/0153112 A1 | 8/2004 | Nissenbaum et al. | |
| 2004/0171905 A1 | 9/2004 | Yu et al. | |
| 2004/0193004 A1 | 9/2004 | Tsubouchi et al. | |
| 2004/0236170 A1 | 11/2004 | Kim | |
| 2005/0033107 A1 | 2/2005 | Tsubouchi | |
| 2005/0101982 A1 | 5/2005 | Ravenscroft et al. | |
| 2005/0131451 A1 | 6/2005 | Kleshinski et al. | |
| 2005/0149093 A1 | 7/2005 | Pokorney | |
| 2005/0154411 A1 | 7/2005 | Breznock et al. | |
| 2005/0209502 A1 | 9/2005 | Schmid et al. | |
| 2005/0251187 A1 | 11/2005 | Beane et al. | |
| 2006/0036313 A1 | 2/2006 | Vassiliades | |
| 2006/0089707 A1 | 4/2006 | Vassiliades et al. | |
| 2006/0099716 A1 | 5/2006 | Tipler et al. | |
| 2006/0142634 A1 | 6/2006 | Anstadt et al. | |
| 2006/0161193 A1 | 7/2006 | Beane et al. | |
| 2007/0088375 A1 | 4/2007 | Beane et al. | |
| 2007/0100363 A1 | 5/2007 | Dollar et al. | |
| 2007/0106315 A1 | 5/2007 | Gregoric et al. | |
| 2007/0134993 A1 | 6/2007 | Tamez et al. | |
| 2007/0167968 A1 | 7/2007 | Pandey | |
| 2007/0167969 A1 | 7/2007 | Pandey | |
| 2007/0173879 A1 | 7/2007 | Pandey | |
| 2007/0197855 A1 | 8/2007 | Richardson et al. | |
| 2007/0208290 A1 | 9/2007 | Pecor et al. | |
| 2007/0265643 A1 | 11/2007 | Beane et al. | |
| 2007/0265656 A1 | 11/2007 | Amplatz et al. | |
| 2008/0009668 A1 | 1/2008 | Cohn | |
| 2008/0009887 A1 | 1/2008 | Cohn | |
| 2008/0009891 A1 | 1/2008 | Cohn | |
| 2008/0076959 A1 | 3/2008 | Farnan et al. | |
| 2009/0012552 A1 | 1/2009 | Pandey et al. | |
| 2009/0082792 A1 | 3/2009 | Koyfman et al. | |
| 2009/0143638 A1 | 6/2009 | Keogh et al. | |
| 2009/0171136 A1 | 7/2009 | Shambaugh, Jr. | |
| 2009/0171386 A1 | 7/2009 | Amplatz et al. | |
| 2010/0305692 A1 | 12/2010 | Thomas et al. | |
| 2011/0118766 A1 | 5/2011 | Reichenbach et al. | |
| 2011/0118829 A1 | 5/2011 | Hoarau et al. | |
| 2011/0118833 A1 | 5/2011 | Reichenbach et al. | |
| 2011/0144680 A1 | 6/2011 | Nguyen et al. | |
| 2011/0160850 A1 | 6/2011 | Bourque | |
| 2011/0245582 A1 | 10/2011 | Zafirelis et al. | |
| 2012/0010455 A1 | 1/2012 | Reichenbach et al. | |
| 2012/0035411 A1 | 2/2012 | LaRose et al. | |
| 2012/0046514 A1 | 2/2012 | Bourque | |
| 2012/0059212 A1 | 3/2012 | Larose et al. | |
| 2012/0059213 A1* | 3/2012 | Spence | A61M 1/3653 600/16 |
| 2012/0059398 A1 | 3/2012 | Pate et al. | |
| 2012/0143141 A1* | 6/2012 | Verkaik | A61M 1/10 604/175 |
| 2012/0165931 A1 | 6/2012 | Bourque | |
| 2012/0226096 A1 | 9/2012 | Callaway et al. | |
| 2012/0253386 A1* | 10/2012 | Rowe | A61B 17/0057 606/213 |
| 2013/0060267 A1 | 3/2013 | Farnan et al. | |
| 2013/0184634 A1 | 7/2013 | McNamara et al. | |
| 2014/0067057 A1 | 3/2014 | Callaway et al. | |
| 2014/0107399 A1* | 4/2014 | Spence | A61M 1/122 600/16 |
| 2014/0200550 A1 | 7/2014 | Farnan et al. | |

(56) References Cited

U.S. PATENT DOCUMENTS

| | | | |
|---|---|---|---|
| 2014/0222040 A1* | 8/2014 | Park | A61B 17/0057 606/153 |
| 2014/0296767 A1* | 10/2014 | Franano | A61M 1/32 604/8 |
| 2015/0032153 A1* | 1/2015 | Quadri | A61B 17/0057 606/215 |
| 2015/0258260 A1 | 9/2015 | Tuseth | |
| 2015/0273124 A1 | 10/2015 | Callaway et al. | |
| 2015/0335802 A1 | 11/2015 | Callaway et al. | |
| 2016/0051738 A1 | 2/2016 | Callaway et al. | |
| 2016/0121033 A1 | 5/2016 | Cotter et al. | |
| 2016/0184561 A9 | 6/2016 | McNamara et al. | |
| 2017/0303958 A1* | 10/2017 | Wu | A61B 17/3417 |
| 2018/0050143 A1 | 2/2018 | Nguyen et al. | |

FOREIGN PATENT DOCUMENTS

| | | |
|---|---|---|
| DE | 20202883 U1 | 7/2002 |
| DE | 10108809 A1 | 9/2002 |
| EP | 1706168 A1 | 10/2006 |
| EP | 2822614 A1 | 1/2015 |
| EP | 2890418 A1 | 7/2015 |
| EP | 3113807 A | 1/2017 |
| JP | 2006528304 A | 12/2006 |
| JP | 2007510522 A | 4/2007 |
| JP | 2009018192 A | 1/2009 |
| JP | 2013510691 A | 3/2013 |
| JP | 6034889 A | 11/2016 |
| WO | 0074747 A1 | 12/2000 |
| WO | 03001980 A2 | 1/2003 |
| WO | 2004014456 A2 | 2/2004 |
| WO | 2005046783 A1 | 5/2005 |
| WO | 2005051838 A2 | 6/2005 |
| WO | 2007038109 A2 | 4/2007 |
| WO | 2008131453 A1 | 10/2008 |
| WO | 2009085243 A2 | 7/2009 |
| WO | 2011060386 A2 | 5/2011 |
| WO | 2011081629 A1 | 7/2011 |
| WO | 2012051454 A2 | 4/2012 |
| WO | 2012119073 A1 | 9/2012 |
| WO | 2013056131 A1 | 4/2013 |
| WO | 2013064529 A1 | 5/2013 |
| WO | 2013134319 A1 | 9/2013 |
| WO | 2014036060 A1 | 3/2014 |
| WO | 2014144085 A1 | 9/2014 |
| WO | 2014149892 A1 | 9/2014 |
| WO | 2015134944 A1 | 9/2015 |
| WO | 2016077444 A1 | 5/2016 |
| WO | 2018039124 A1 | 3/2018 |

OTHER PUBLICATIONS

Thompson, "An overview of nickel-titanium alloys used in dentistry", International Endodontic Journal, vol. 33, 2000, pp. 297-310.

Wikipedia, "Nickel titanium", Retrieved from the Internet:< URL: https://en.wikipedia.org/wiki/Nickel_titanium retrieved on Mar. 10, 2013, Mar. 10, 2013, 9 pages.

* cited by examiner

MINIMALLY INVASIVE METHODS AND DEVICES FOR VENTRICULAR ASSIST DEVICE IMPLANTATION

CROSS-REFERENCE TO RELATED APPLICATIONS

The present application claims the benefit of U.S. Provisional Application Ser. No. 62/463,337, filed on Feb. 24, 2017, which is incorporated by reference herein in its entirety for all purposes.

BACKGROUND

Ventricular assist devices, known as VADs, often include an implantable blood pump and are used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term destination therapy. A patient may also use a VAD while recovering from heart surgery. Thus, a VAD can supplement a weak heart (i.e., partial support) or can effectively replace the natural heart's function.

In many instances, blood from a ventricle of the heart is extracted through an aperture or opening formed in the wall of the ventricle and pumped by a VAD to the patient's circulatory system. For example, a left ventricular assist device (LVAD) can extract blood from the patient's left ventricle and pump the blood into the patient's ascending aorta. A VAD can be implanted adjacent to the heart, in contact with the heart, or in a remote location such as the abdomen. Existing approaches for fluidly coupling a VAD with the heart include removing a portion of the heart wall via coring or cutting to create an opening, suturing an annular cuff to the exterior of the heart wall opening, and aligning the VAD with the annular cuff. The cuff attachment procedure however is substantially invasive, both in terms of the amount of access required and the localized trauma inflicted on the heart wall, and can be a time consuming and complicated procedure that is costly. As such, improved methods and devices for VAD implantation may be desirable.

BRIEF SUMMARY

Improved implantable structures and methods for fluidly coupling a VAD with a ventricle, and related surgical assemblies and methods, are described. In many embodiments, a distal end of a delivery device is penetrated through a ventricular wall through an aperture into a ventricle. A self-expandable coupler, such as an anchor, stent, scaffold, shunt, or other expandable structure, is deployed from the delivery device to engage the aperture and form an access conduit for extraction of blood from the ventricle. The delivery device is then removed via the aperture, leaving the coupler attached to the heart wall. An inlet fluid channel for the VAD can then be coupled with the coupler to place the VAD in fluid communication with the ventricular chamber via the coupler conduit. In contrast with existing approaches that require substantial access to the heart and induce substantial localized trauma to the heart via associated coring, cutting, and/or suturing, the implantation of a self-expandable coupler via a delivery device as described herein can be accomplished faster, simpler, and less invasively with reduced access to the heart. The procedure may result in a smaller ventricle aperture (defect) that is dilated so as to minimize localized trauma to the heart wall. Further, the expandable structure of the coupler allows accommodation in a variety of VAD inlet conduit sizes and shapes as well as varying aperture diameters.

Thus, in one aspect, a method of implanting a ventricular assist device in a patient is provided. The method includes penetrating a distal end of a delivery device through a wall of a heart into a ventricle of the heart through an aperture having a diameter in the wall. Penetrating may comprise dilating the aperture with the delivery device, such as a catheter, so as to expand the diameter of the aperture while minimizing complications such as excessive blood leakage or unintended damage to adjacent structures or vessels. An expandable coupler is deployed from the delivery device so that the coupler engages the aperture and forms a conduit for a flow of blood from the ventricle. The delivery device is removed from the ventricle by retracting the delivery device through the aperture. The ventricular assist device is coupled to the coupler to receive the flow of blood from the ventricle and pump the flow of blood to assist circulation in the patient.

In many embodiments of the method, the coupler engages an inner surface of the heart wall adjacent to the aperture and/or an outer surface of the heart wall adjacent to the aperture. For example, the method of implanting a ventricular assist device in a patient can include (a) engaging an inner surface of the wall of the heart with an inner flange of the coupler that protrudes radially relative to the aperture, and/or (b) engaging an outer surface of the wall of the heart with an outer flange of the coupler that protrudes radially relative to the aperture. Methods include accommodating ingrowth of tissue from the heart wall into the coupler. For example, the method can include accommodating ingrowth of tissue from at least one of (a) the inner surface of the wall into the inner flange of the coupler, (b) the outer surface of the wall into the outer flange of the coupler, and/or (c) a surface of the aperture of the wall into a portion of the coupler engaged with the aperture. Tissue ingrowth into the coupler can provide for a natural blood contact surface and compressive seal barrier that further minimizes blood leakage as well as clot or thrombus formation.

Deploying the self-expanding coupler from the delivery device can include reconfiguring the delivery device to release the coupler from a delivery configuration so that the coupler self-expands to a deployed configuration. Any suitable approach can be used to release the coupler. For example, reconfiguring the delivery device to release the coupler from the delivery configuration can include retracting a sheath from a retention configuration in which the sheath retains the coupler in the delivery configuration to a release configuration in which the coupler is not retained by the sheath.

In many embodiments of the method, the coupler is partially released so that an inner flange of the coupler is expanded within the ventricle and then retracted to bring the inner flange into engagement with the ventricular wall prior to release of the rest of the coupler. For example, reconfiguring the delivery device to release the coupler from the delivery configuration can include retracting the sheath from the retention configuration to an inner flange release configuration in which the inner flange of the coupler protrudes radially from the delivery device and a portion of the coupler is retained by the sheath. Deploying the coupler from the delivery device can include retracting the delivery device with the sheath in the inner flange release configuration to bring the inner flange into engagement with the inner surface of the wall of the heart.

In many embodiments of the method, the coupler can be configured to block flow of blood through the aperture prior to coupling of the VAD with the coupler. For example, the coupler can include a flow control portion reconfigurable from a flow blocking configuration to a flow accommodating configuration. The method can further include (a) blocking flow of blood through the conduit via the flow control portion in the flow blocking configuration prior to coupling the ventricular assist device to the coupler, and (b) reconfiguring the flow control portion from the flow blocking configuration to the flow accommodating configuration to accommodate the flow of blood from the ventricle to the ventricular assist device for pumping to assist circulation in the patient. Any suitable approach can be used to reconfigure the flow control portion from the flow blocking configuration to the flow accommodating configuration. For example, reconfiguring the flow control portion from the flow blocking configuration to the flow accommodating configuration can include engaging an inlet conduit of the ventricular assist device with the flow control portion to deform the flow control portion from the flow blocking configuration to the flow accommodating configuration.

Any suitable approach can be used to fluidly couple the VAD with the ventricle via the coupler. For example, coupling the ventricular assist device to the coupler can include inserting an inlet conduit of the ventricular assist device into the conduit of the coupler so that inlet conduit forms a sealed attachment with the coupler. The coupler has an inlet portion that extends into the ventricle. The inlet portion that extends into the ventricle can have any suitable configuration (e.g., geometry, shape, size, etc.). For example, a portion of the conduit formed by the inlet portion can have a tapering cross-sectional area. The inlet portion can have an inlet edge shaped to form one or more valleys between adjacent peaks. The one or more valleys can be configured to maintain fluid communication between the ventricle and the conduit if contact occurs between the inlet edge and an inner surface of the ventricle. The inlet portion can have one or more features that interface with the coupler and accommodate insertion of the inlet portion into the conduit of the coupler and prevent extraction of the inlet portion from the conduit of the coupler without the application of significant extraction force to the inlet portion. For example, the inlet portion can include a one-way locking catch and/or hook structure that that interfaces with the coupler and accommodates insertion of the inlet portion into the conduit of the coupler and prevents extraction of the inlet portion from the conduit of the coupler without the application of significant extraction force to the inlet portion. Advantageously, the aperture or puncture diameter is smaller than the inlet portion of the coupler in the deployed configuration for a less invasive procedure and larger opening inlet.

In another aspect, a surgical assembly for coupling a ventricular assist device with a ventricle of a heart of a patient is disclosed. The surgical assembly includes a self-expandable implantable coupler and a delivery device for implanting the coupler. The implantable coupler is reconfigurable between a delivery configuration and a deployed configuration. The coupler is configured to expand from the delivery configuration to engage an aperture through a wall of the ventricle and form a conduit for a flow of blood from the ventricle. The coupler is further configured to couple with a ventricular assist device to transfer the flow of blood to the ventricular assist device for pumping to assist in circulation of the patient. The delivery device is configured for implanting the coupler. The delivery device includes a distal end portion shaped for penetration through the wall of the ventricle to form the aperture and a repositionable sheath having a retention configuration in which the sheath retains the coupler in the delivery configuration and a release configuration accommodating release of the coupler via self-expansion of the coupler from the delivery configuration to the deployed configuration. The delivery device may comprise a catheter configured to dilate the aperture so as to expand a diameter of the aperture.

In many embodiments of the surgical assembly, the coupler is configured to interface with the heart wall adjacent to the aperture. For example, in many embodiments, the coupler has (a) an inner flange that protrudes radially relative to the aperture and is configured to interface with an inner surface of the wall of the ventricle, and/or (b) an outer flange that protrudes radially relative to the aperture and is configured to interface with an outer surface of the wall of the ventricle. The outer and/or inner flange can have any suitable configuration. For example, the shape of the outer and/or inner flange may further inhibit mal-positioning of the inlet portion. The coupler is configured to accommodate ingrowth of tissue from the heart wall. For example, the coupler can include one or more material layers configured to accommodate ingrowth of tissue from at least one of (a) the inner surface of the wall into a portion of the material layer disposed in the inner flange of the coupler, (b) the outer surface of the wall into a portion of the material layer disposed in the outer flange of the coupler, and/or (c) a surface of the aperture in the wall into a portion of the material layer disposed in a portion of the coupler engaged with the aperture. Additionally, at least one anchor may be provided on the outer flange to further facilitate coupler engagement with the wall the ventricle.

In many embodiments, the surgical assembly is configured to partially deploy the coupler to deploy an inner flange of the coupler within the ventricle for subsequent retraction into engagement with the heart wall prior to deployment of the rest of the coupler. For example, in many embodiments of the surgical assembly, the repositionable sheath has an inner flange release configuration in which the inner flange of the coupler outwardly protrudes from the delivery device and a portion of the coupler is constrained by the repositionable sheath to enable deployment of the inner flange within the ventricle and subsequent retraction of the delivery device to bring the inner flange into engagement with the inner surface of the wall of the ventricle prior to deployment of the rest of the coupler.

In many embodiments of the surgical assembly, the coupler is configured to block flow of blood through the coupler conduit prior to coupling a VAD with the coupler. For example, in many embodiments, the coupler includes a flow control portion reconfigurable from a flow blocking configuration that blocks flow of blood through the conduit prior to coupling of the ventricular assist device to the coupler to a flow accommodating configuration that accommodates the flow of blood from the ventricle to the ventricular assist device for pumping to assist circulation in the patient. The flow control portion can be reconfigurable from the flow blocking configuration to the flow accommodating configuration via engagement of an inlet conduit of a ventricular assist device with the flow control portion to reconfigure the flow control portion. The flow control portion can have any suitable configuration. For example, the flow control portion may comprise a membrane or valve member.

The coupler included in the surgical assembly can have any suitable configuration for fluidly coupling the VAD with the ventricle. For example, the coupler can be configured for insertion of an inlet conduit of the VAD into the conduit of the coupler so that a sealed attachment is formed between the inlet conduit of the VAD and the coupler. In many embodiments of the surgical assembly, the coupler has an inlet portion configured to extend into the ventricle. The inlet portion that extends into the ventricle can have any suitable configuration. For example, a portion of the conduit formed by the inlet portion can have a tapering cross-sectional area. The inlet portion can have an inlet edge shaped to form one or more valleys between adjacent peaks. The one of more valleys can be configured to maintain fluid communication between the ventricle and the conduit if contact occurs between the inlet edge and an inner surface of the ventricle. The inlet portion can have one or more features that interface with the coupler and accommodate insertion of the inlet portion into the conduit of the coupler and prevent extraction of the inlet portion from the conduit of the coupler without the application of significant extraction force to the inlet portion. For example, the inlet portion can include a one-way locking catch and/or hook structure that that interfaces with the coupler and accommodates insertion of the inlet portion into the conduit of the coupler and prevents extraction of the inlet portion from the conduit of the coupler without the application of significant extraction force to the inlet portion. Minimally invasive catheter delivery and the self-expanding structure of the coupler allows for the diameter of the aperture to be smaller than a diameter of the inlet edge of the coupler inlet portion in the deployed configuration. The inlet portion of the coupler may form a funnel or cone shape having a variable angle opening (e.g., wide funnel) or any other suitable shape, size, or angle orientation.

The coupler included in the surgical assembly can further comprise a mesh or coating layer supported by the frame (e.g., coupled to an inner or outer surface of the frame). The mesh layer or coating may accommodate ingrowth of tissue into the coupler to create a natural tissue interface that provides improved sealing with the aperture and reduces any blood leakage. The coupler may additionally or alternatively include a rigid or semi-flexible support section in a portion of the conduit that extends within the aperture in the wall of the ventricle. This rigid support, tube, or bore may be integral with the coupler or an additional structural support so that the coupler has sufficient rigidity to prevent collapse of the coupler and maintain patency and access.

In another aspect, an implantable coupler for coupling a ventricular assist device with a ventricle of a heart of a patient is disclosed. The implantable coupler includes a self-expandable frame, such as a woven nickel titanium tube, and a material layer, such as a polyester mesh, that accommodates tissue ingrowth (e.g., endothelialization) from the heart wall for stabilization. The frame is configured to expand from a collapsed configuration sized to be inserted through an aperture in a wall of the ventricle to a deployed configuration in which the frame (a) engages the aperture, (b) expands or dilates the aperture, (c) forms a conduit for a flow of blood from the ventricle, (d) forms an inner flange that protrudes radially relative to the aperture and is configured to interface with an inner surface of the wall of the ventricle, and (e) forms an outer flange that protrudes radially relative to the aperture and is configured to interface with an outer surface of the wall of the ventricle. The material layer is supported by the frame and accommodates ingrowth of tissue into the material layer from at least one of (a) the inner surface of the wall of the ventricle into a portion of the material layer disposed in the inner flange of the coupler, (b) the outer surface of the wall of the ventricle into a portion of the material layer disposed in the outer flange of the coupler, and/or (c) a surface of the aperture in the wall of the ventricle into a portion of the material layer disposed in a portion of the coupler engaged with the aperture.

In many embodiments, the implantable coupler is configured to block flow of blood through the coupler conduit prior to coupling a VAD with the coupler. For example, the implantable coupler can include a flow control portion reconfigurable from a flow blocking configuration that blocks flow of blood through the conduit prior to coupling of the ventricular assist device to the coupler to a flow accommodating configuration that accommodates the flow of blood from the ventricle to the ventricular assist device for pumping to assist circulation in the patient. The flow control portion can have any suitable configuration. For example, the flow control portion can be reconfigurable from the flow blocking configuration to the flow accommodating configuration via engagement of an inlet conduit of the ventricular assist device with the flow control portion to reconfigure the flow control portion.

The implantable coupler can have any suitable configuration for fluidly coupling the VAD with the ventricle. For example, the coupler can be configured for insertion of an inlet conduit of the ventricular assist device into the conduit of the coupler so that a sealed attachment is formed between the inlet conduit and the coupler. In many embodiments, the implantable coupler has an inlet portion configured to extend into the ventricle. The inlet portion that extends into the ventricle can have any suitable configuration. For example, a portion of the conduit formed by the inlet portion can have a tapering cross-sectional area forming a funnel shape in the deployed configuration. The inlet portion can have an inlet edge shaped to form one or more valleys between adjacent peaks. The one of more valleys can be configured to maintain fluid communication between the ventricle and the conduit if contact occurs between the inlet edge and an inner surface of the ventricle. The inlet portion can have one or more features that interface with the coupler and accommodate insertion of the inlet portion into the conduit of the coupler and prevent extraction of the inlet portion from the conduit of the coupler without the application of significant extraction force to the inlet portion. For example, the inlet portion can include a one-way locking catch and/or hook structure that that interfaces with the coupler and accommodates insertion of the inlet portion into the conduit of the coupler and prevents extraction of the inlet portion from the conduit of the coupler without the application of significant extraction force to the inlet portion.

The above presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later. For a fuller understanding of the nature and advantages of the present invention, reference should be made to the ensuing detailed description and accompanying drawings.

DETAILED DESCRIPTION

The implantable couplers for fluidly coupling a VAD with a ventricle described herein can be used in lieu of existing attachment cuffs. The implantable couplers can be delivered via a suitable catheter or similar delivery tool. The myocardial wall can be punctured and/or slit and the coupler delivered into the resulting aperture in the myocardial wall and expanded. Alternatively, the delivery tool can have a distal end configured to be penetrated through the myocardial wall to form the aperture into which the coupler is implanted. The coupler forms a conduit through which an inlet of a VAD is placed in fluid communication with the ventricle. In many embodiments, the conduit is sufficiently rigid to prevent collapse and maintain access. In many embodiments, the coupler has an inner flange that extends radially from the coupler and interfaces with an inner surface of the ventricle and an outer flange that extends radially from the coupler and interfaces with an outer surface of the myocardial wall. In many embodiments, the inner and outer flanges inhibit and/or prevent migration of the coupler prior to and subsequent ingrowth of tissue from the myocardial wall into the coupler.

In many embodiments, the implantable couplers disclosed herein are configured to provide numerous benefits relative to existing attachment cuffs. For example, in many embodiments, the coupler has an inlet portion that extends into the ventricle. A portion of the conduit within the inlet portion can have a larger inlet area than a portion of the conduit passing through the aperture in the myocardial wall, thereby providing improved flow characteristics in conjunction with a small puncture site that does not require coring, a suture ring, and all of the associated procedure time and complexity. The elimination of coring is also compatible with a tight compressive seal between the coupler and an inlet cannula of a VAD. In many embodiments, the coupler includes a fibrotic mesh and nitinol structure that effectively induces endothelialization and stabilization. Engagement of the endothelial layer by the expanded coupler creates a natural blood contact surface that inhibits clotting and thrombus formation. In many embodiments, the end of the conduit that exits the heart is configured to interlock with a VAD and can include a valve or membrane feature that allow an off-bypass procedure or could be open and used with a bypass procedure. Employment of the couplers disclosed herein can dramatically reduce procedure times and complexity and can be delivered in a minimally or less invasive procedure.

Figure 1:
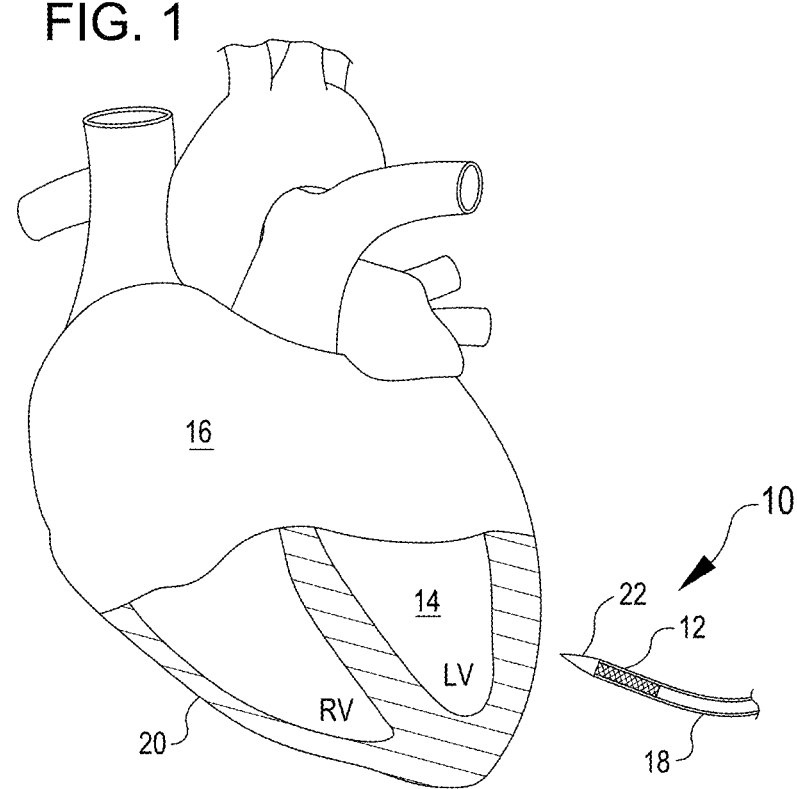
FIG. 1 shows a surgical assembly that includes an implantable coupler for fluidly coupling a VAD with a ventricle and a delivery device positioned for penetration through a heart wall into the ventricle to form an aperture in the heart wall in which the coupler is implanted, in accordance with many embodiments.

Referring now to the drawings, in which like reference numerals represent like parts throughout the several views, FIG. 1 shows the distal end of a surgical assembly 10 that includes an implantable coupler 12 for fluidly coupling a VAD with a ventricle 14 of a heart 16 and a delivery device 18 positioned for penetration through a heart wall 20 into the ventricle 14 to form an aperture in the heart wall 20 in which the coupler 12 is implanted. In the illustrated embodiment, the distal end of the delivery device 18 includes a distal tip member 22 having a suitable tapered shape for penetration through the heart wall 20 to form an aperture in which the coupler 12 is implanted.

Figure 2:
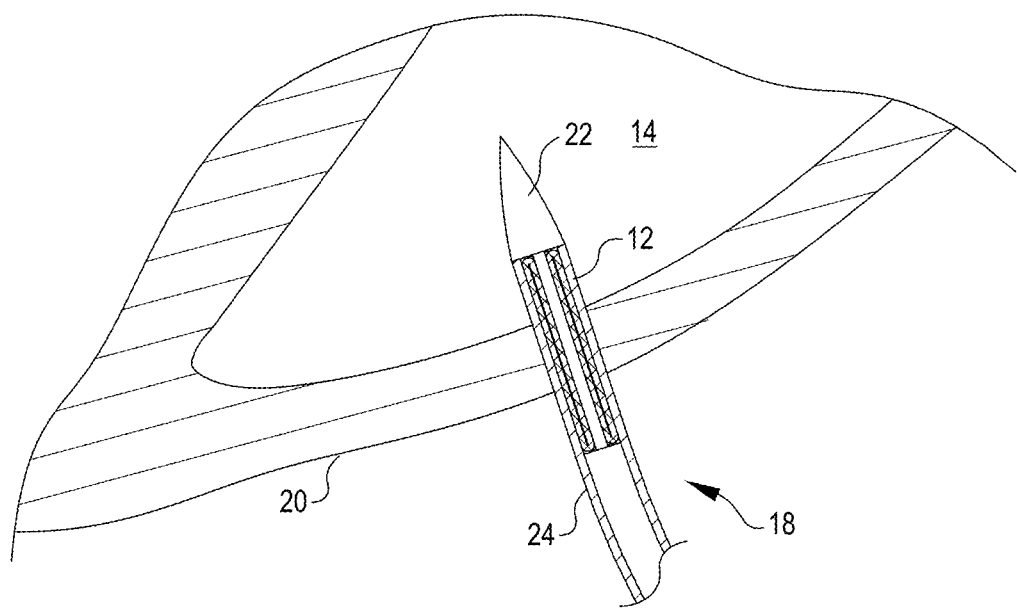
FIG. 2 shows the surgical assembly of FIG. 1 penetrated through the heart wall to a position for deployment of the coupler.

FIG. 2 shows the delivery device 18 penetrated through the heart wall 20 to a position for deployment of the coupler 12 into a resulting aperture through the heart wall 20. In many embodiments, the delivery device 18 includes a repositionable sheath 24 that retains the coupler 12 in a collapsed delivery configuration during penetration of a distal portion of the delivery device 18 through the heart wall 20. In the illustrated configuration, the sheath 24 is shown in a retention configuration in which a distal end of the sheath 24 is interfaced with the distal tip member 22, thereby enclosing the coupler 12 within a coupler transport section of the delivery device 18. In the illustrated embodiment, the sheath 24 has an outer surface that aligns with an outer surface of the distal tip member 22 so that a portion of the sheath 24 can be passed through the aperture in the heart wall 20 formed by the penetration of the distal tip member 22.

Figure 3:
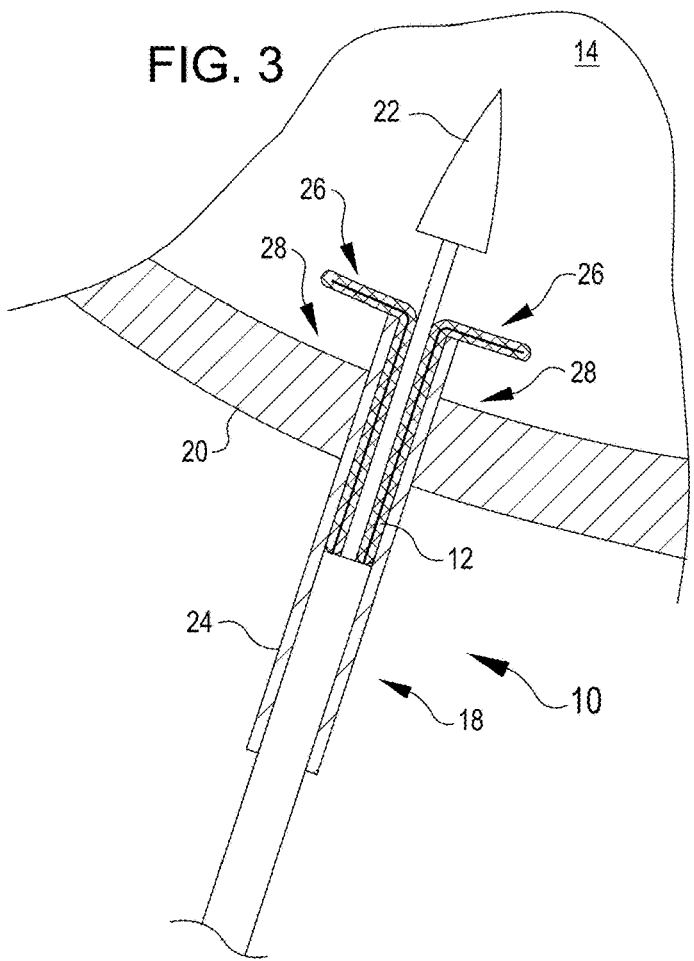
FIG. 3 shows the surgical assembly of FIG. 1 with the coupler partially deployed to deploy an inner flange of the coupler within the ventricle for subsequent retraction of the surgical assembly to bring the inner flange into engagement with an inner surface of the heart wall surrounding the aperture.
Figure 4:
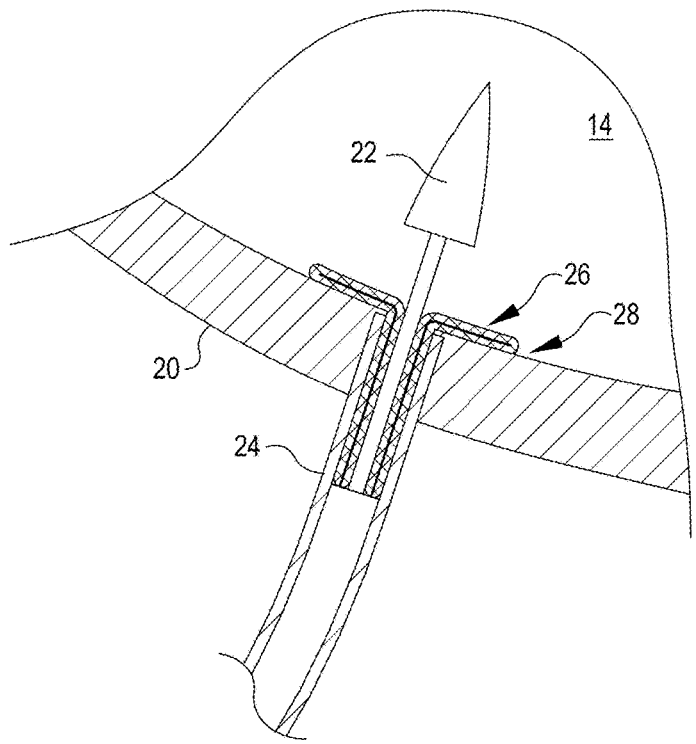
FIG. 4 shows the surgical assembly of FIG. 1 in the configuration of FIG. 3 with the inner flange interfaced with the inner surface of the heart wall surrounding the aperture via retraction of the surgical assembly from the position of FIG. 3.

FIG. 3 shows the surgical assembly 10 with the coupler 12 partially deployed to deploy an inner flange 26 of the coupler 12 within the ventricle 14 for subsequent retraction of the surgical assembly 10 to bring the inner flange 26 into engagement with an inner surface 28 of the heart wall 20 surrounding the aperture formed by the penetration of the distal tip member 22. In the illustrated configuration, the partial deployment of the coupler 12 to deploy the inner flange 26 within the ventricle 14 is accomplished by a partial retraction of the sheath 24 to an inner flange release configuration in which the inner flange 26 is not retained by the sheath 24 and a remaining portion of the coupler 12 remains retained by the sheath 24. By partially deploying the coupler 12 to deploy the inner flange 26 within the ventricle, the surgical assembly 10 can be subsequently retracted away from the ventricle 14 to engage the inner flange 26 with the inner surface 28 of the heart wall 20, thereby generating a tactile feedback indicative of positioning of the coupler 12 for subsequent completion of the deployment of the coupler 12 from the delivery device 18. FIG. 4 shows the surgical assembly 10 with the inner flange 26 interfaced with the inner surface 28 of the heart wall 20 surrounding the aperture via retraction of the surgical assembly 10 from the position shown in FIG. 3.

Figure 5:
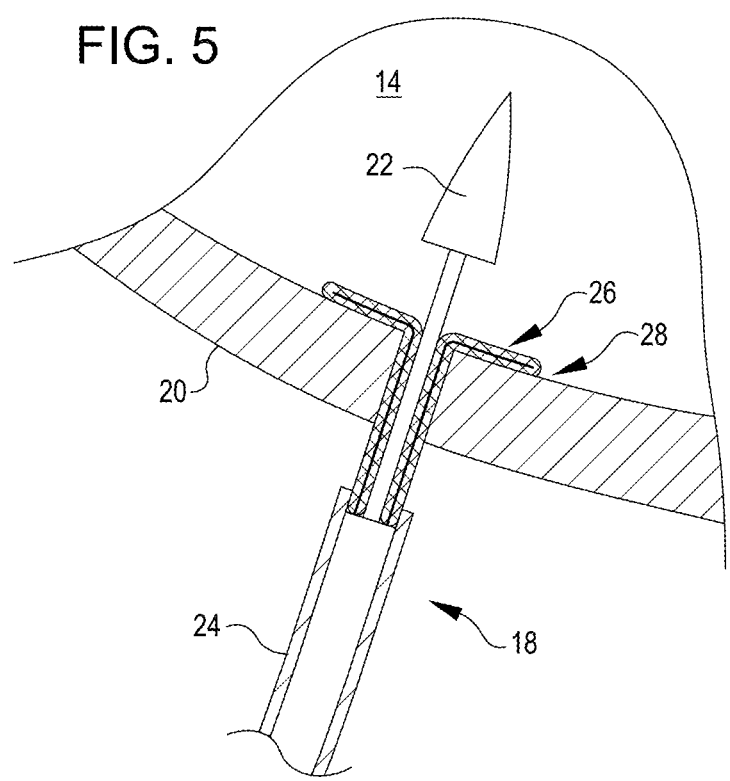
FIG. 5 illustrates further deployment of the coupler of the surgical assembly of FIG. 1 from the configuration of FIG. 4.
Figure 6:
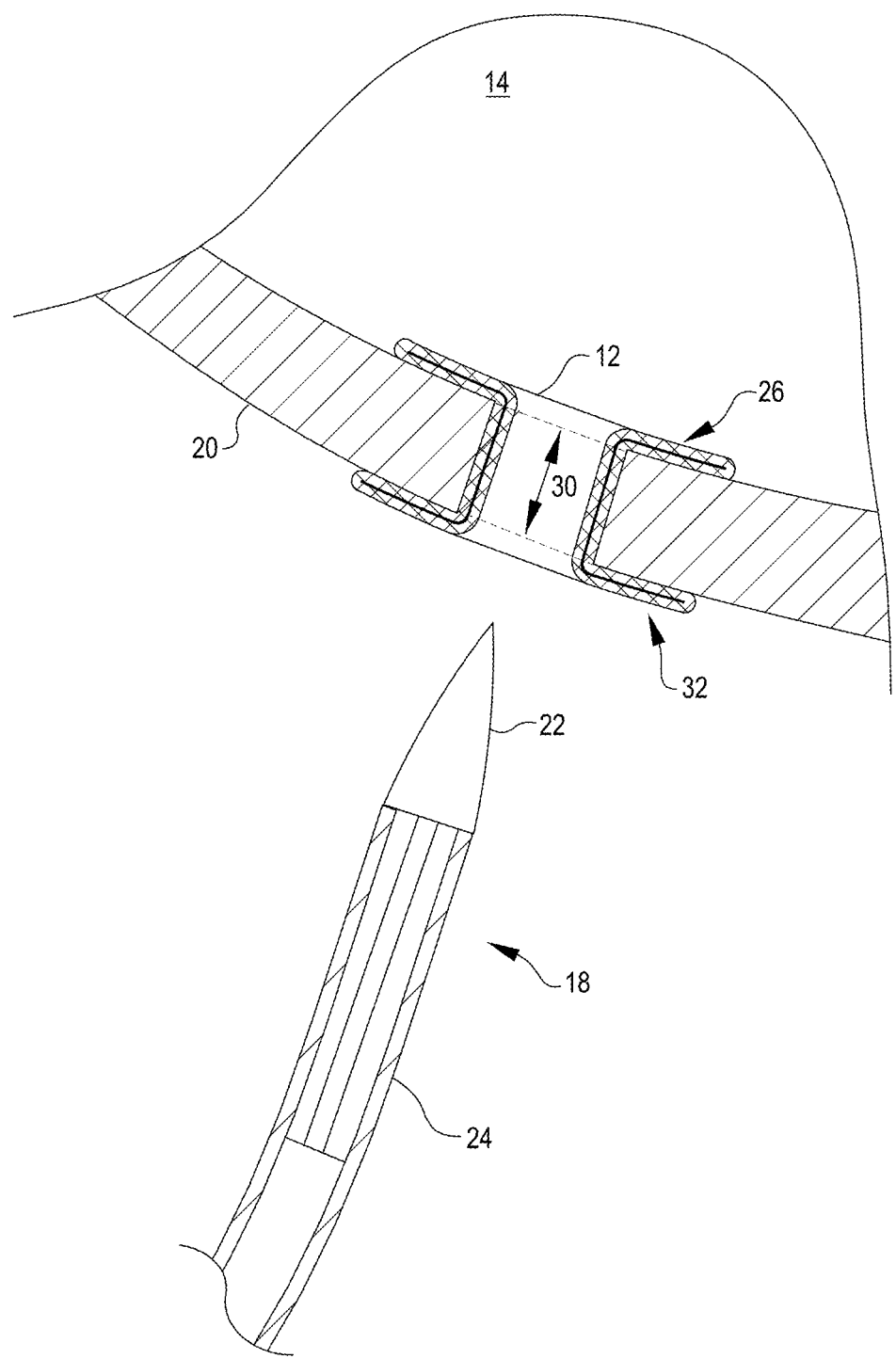
FIG. 6 shows the surgical assembly of FIG. 1 with the coupler fully deployed and the delivery device removed from the aperture through the coupler conduit.

FIG. 5 illustrates further deployment of the coupler 12 from the delivery device 18. The further deployment of the coupler 12 is accomplished by further retracting the sheath 24 from the inner flange release configuration shown in FIG. 3 and FIG. 4. FIG. 6 shows the coupler 12 fully deployed and the delivery device 18 removed. In the fully deployed configuration, the coupler 12 forms a conduit 30, the inner flange 26, and an outer flange 32, which engages an outer surface of the heart wall 20 surrounding the aperture. In many embodiments, the coupler 12 self-expands when released from the collapsed delivery configuration to a deployed configuration in which the coupler 12 engages the aperture, expands the diameter of the aperture, and forms the conduit 30 through which the VAD is placed in fluid communication with the ventricle 14.

Figure 7:
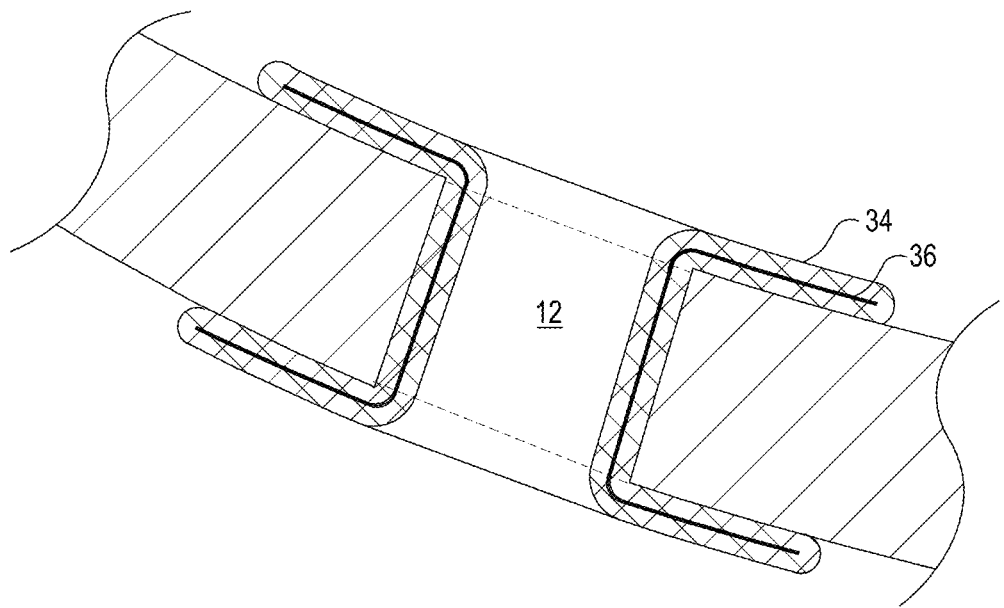
FIG. 7 shows a cross-sectional view of the coupler of the surgical assembly of FIG. 1 in a fully deployed configuration.

FIG. 7 shows a cross-sectional view of the coupler 12 in the deployed configuration. In the illustrated embodiment, the coupler 12 includes a self-expanding frame 34 and a fibrotic mesh 36 retained by the frame 34 and/or coating (not shown). Suitable materials for the self-expanding frame include, but are not limited to, shape-memory materials (e.g. nitinol), stainless steel, flexible polymers, gold, titanium, cobalt-chromium alloy, tantalum alloy, and more. Typically the material will be flexible, supportive, capable of expansion, and/or biocompatible. Examples of self-expandable structures, including self-expanding frames, meshes, and/or coatings, suitable for use in the present invention are disclosed in commonly owned U.S. Pat. Nos. 9,364,593; 9,358,329; 9,039,724; 8,961,556; 8,454,633; 8,313,505; 8,034,061; 6,682,546; 6,682,546; 6,599,308; 6,447,531; 6,168,622; 5,944,738; 5,846,261; and 5,725,552, all of which are incorporated herein by reference in their entirety for all purposes. Additional exemplars of self-expandable structures are disclosed in U.S. Pat. Nos. 8,951,223 and 8,882,697 and U.S. Patent Publication No. 2016/0184561, all of which are incorporated herein by reference in their entirety for all purposes. Any suitable material can be used in the fibrotic mesh 36 or coating, such as polyester, polyurethane, a fabric or graft material, and the like. In various embodiments, the coupler includes a coating. The coating may be a biocompatible coating and/or a drug eluting coating. The engagement of the frame 34 and the fibrotic mesh 36 and/or coating with the heart wall 20 induces endothelialization and stabilization of the coupler 12 relative to the heart wall 20, and may also minimize blood clotting and inflammation.

The self-expandable implantable structures of the present invention may be formed from a braided fabric formed of a plurality of wire strands having a predetermined relative orientation with respect to one another. However, it will be appreciated that the self-expandable structures may also be formed using various other techniques. For example, the self-expandable structure could be etched or laser cut from a tube such as to form an interstice geometry, or the expandable structure could comprise a material coupled to a scaffolding structure or a plurality of slices of a tubular member coupled together, such as via gluing. Moreover, it will be appreciated that the self-expandable structure may comprise one or more layers of materials. Although the term "strand" is discussed herein, "strand" is not meant to be limiting, as it is understood the fabric may comprise one or more wires, cords, fibers, yarns, filaments, cables, threads, or the like, such that such terms may be used interchangeably. For example, the expandable structure is a metal fabric including a plurality of strands, such as two sets of essentially parallel generally helical strands, with the strands of one set having a "hand", i.e., a direction of rotation, opposite that of the other set. The strands may be braided, interwoven, or otherwise combined to define a generally tubular fabric.

The pitch of the strands (i.e., the angle defined between the turns of the strands and the axis of the braid) and the pick of the fabric (i.e., the number of wire strand crossovers per unit length) may be adjusted as desired for a particular application. For example, the pick count could be in range from about 20 picks/inch to 150 picks/inch. The wire strands of the metal fabric used in one embodiment of the present method may be formed of a material that is both resilient and can be heat treated to substantially set a desired shape. One factor in choosing a suitable material for the wire strands is that the wires retain a suitable amount of the deformation induced by the molding surface (as described below) when subjected to a predetermined heat treatment and elastically return to said molded shape after substantial deformation. For example, each layer of the self-expandable structure may comprise 36-144 wire strands ranging in diameter from about 0.001 to 0.012 in. formed of a shape memory alloy or highly elastic material braided so as to define fenestrations with an area of about 0.00015 to 0.1 sq. in. Inner and outer braided layers may have pitch angles that are about equal to obtain desirable collapse and expansion characteristics, such as maintaining a uniform overall length.

One class of materials which meets these qualifications is so-called shape memory materials. One particularly preferred shape memory alloy for use in the present method is Nitinol. NiTi alloys are also very elastic, superelastic, or pseudoelastic. This elasticity may allow the coupler structure to return to a preset expanded configuration for deployment following passage in a collapsed delivery configuration form through a delivery catheter. The structure may also take advantage of shape memory properties, e.g., by setting specific shapes above and below a desired transition temperature of the material. It will be appreciated that the expandable structure may comprise various materials other than Nitinol that have elastic properties, such as spring stainless steel, trade named alloys such as Elgiloy, or Hastalloy, Phynox, MP35N, CoCrMo alloys or a mixture of metal and polymer fibers. Polymer fibers may include monofilaments or multifilament yarns ranging from about 10-400 denier. Individual filaments may range from about 0.25 to 10 denier. Polymers may be composed of PET (Dacron), polyester, polypropylene, polyethylene, HDPE, polyurethane, silicone, PTFE, polyolefins and ePTFE. The metal and plastic fibers may be combined in the same layer, or tubular layers may be constructed in such a manner that each layer is made from a different material. The polymer layer may be a multifilament braided layer or may be composed of at least one filament or yarn wound about a mandrel with a pitch and diameter similar to other adjacent layers and may be positioned about or inside another adjacent layer or between adjacent layers. Depending on the individual material selected, the wire strand diameter, number of wire strands, and/or pitch may be altered to achieve the desired properties of the self-expandable structure. Moreover, other suitable materials include those that are compatible with magnetic resonance imaging (MM), as some materials may cause heat or torque resulting from performing MRI, and some materials may distort the MRI image. Thus, metallic and/or non-metallic materials that reduce or eliminate these potential problems resulting from using MM may be employed.

In forming a self-expandable structure, an appropriately sized piece of the fabric is cut from a larger piece of fabric which is formed, for example, by braiding wire strands to form a long tubular braid. When cutting the fabric to the desired dimensions, care should be taken to ensure that the fabric will not unravel. One can solder, braze, weld, coat, glue, clamp, tie or otherwise affix the ends of the desired length together (e.g., with a biocompatible cementitious organic material). In addition, a plurality of layers of material could be separately woven into tubular members, with each tubular member coaxially disposed within another tubular member. For further discussion regarding an exemplary multi-layer device and techniques for fabricating such a device, see U.S. Patent Appl. Publ. No. 2007/0265656 to Amplatz et al., which is hereby incorporated in its entirety by reference. Still further, the expandable structure may be coated with a suitable agent, filled with a polyester fiber, or include a mesh fabric.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element should be selected to deform the fabric into substantially the desired shape when unconstrained. Once the molding element is assembled with the metal fabric generally conforming to a molding surface of that element, the fabric can be subjected to a heat treatment while it remains in contact with that molding surface. After the heat treatment, the fabric is removed from contact with the molding element and will substantially retain its shape in a deformed state.

Once a preselected shape has been formed, the self-expandable structure may be used for anchoring across a myocardial wall so as to fluidly coupling a VAD with a ventricle. In operation, a catheter, sheath, or other suitable delivery device may be positioned through a wall of a heart into a ventricle of the heart through an aperture having a diameter in the wall. Penetrating may additionally comprise dilating the aperture with the delivery device so as to expand the diameter of the aperture while minimizing complications such as excessive blood leakage or unintended damage to adjacent structures or vessels. The self-expandable structure is deployed from the delivery device so that it engages the aperture and forms a conduit for a flow of blood from the ventricle. The delivery device is removed from the ventricle by retracting the delivery device through the aperture. The ventricular assist device is coupled to the self-expandable structure to receive the flow of blood from the ventricle and pump the flow of blood to assist circulation in the patient. One will appreciate that access can be provided with techniques which do not require dilating the aperture. In some embodiments, access may be provided by creating a defect site or aperture large enough to receive the delivery device working end without dilation. For example, the ventricle wall may be cored with a coring tool.

The delivery device can take any suitable shape, such as an elongate flexible metal shaft or hypotube or metal braided polymer tube, optionally having a distal end for engagement with the self-expandable structure (e.g., threaded bore, clamp arrangement, or like detachable securing means) so as to allow it to retain the self-expandable structure until the desired positioning (or repositioning) is achieved across the heart wall. The self-expandable structure can be collapsed into its reduced diameter configuration and inserted into the lumen of the delivery catheter. The delivery device can also be used to urge the self-expandable structure through the lumen of a catheter/sheath for subsequent deployment. The collapsed configuration may be of any shape suitable for easy passage through the lumen of a catheter and proper deployment out the distal end of the catheter. For example, the self-expandable structure may have a relatively elongated collapsed configuration wherein the structure is stretched along its axis. This collapsed configuration can be achieved simply by stretching the structure generally along its axis, which will tend to collapse the expanded diameter portions of the structure inwardly toward the structure's axis. In this regard, these devices are not unlike "Chinese handcuffs", which tend to constrict in diameter under axial tension.

Once the self-expandable structure is properly positioned and deployed within the aperture of the heart wall, the shaft of the delivery device can be removed from the heart by simply retracting the delivery device. For further discussion regarding a delivery device and methods that may be used to deploy a self-expandable device according to various aspects of the present invention, see U.S. patent application Ser. No. 11/966,397 to Adams et al., which is hereby incorporated in its entirety by reference. Although the self-expandable structure will tend to resiliently return to its initial expanded configuration, i.e., its shape prior to being collapsed for passage through the catheter, it should be understood that it might not always return entirely to that shape. Nonetheless, the self-expandable structure would be properly deployed because it would engage the aperture of the heart wall to seat the structure therein.

Figure 8:
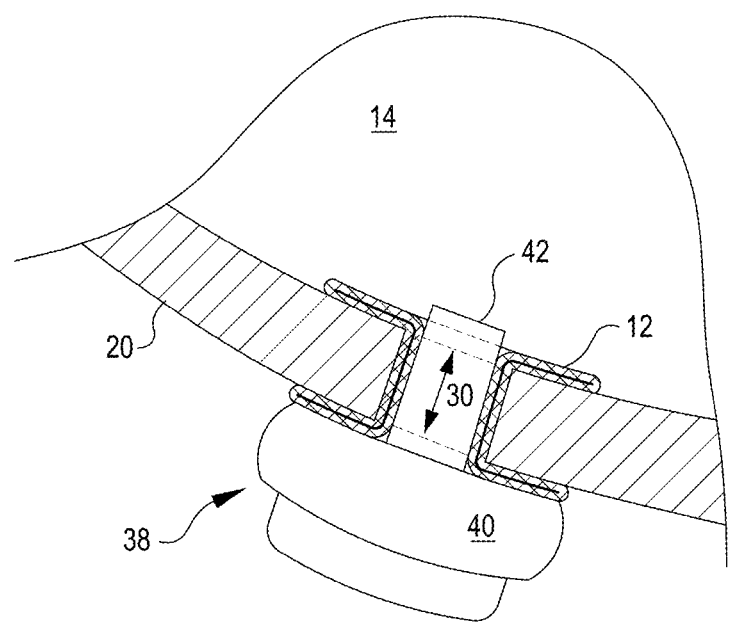
FIG. 8 shows a VAD coupled with an implanted coupler of the surgical assembly of FIG. 1.

FIG. 8 shows a VAD 38 coupled with an implanted coupler 12. In the illustrated embodiment, the VAD 38 includes a pump assembly 40 and an inlet cannula 42, which extends from the pump assembly 40 and provides an inlet fluid channel by which blood flow is pumped from the ventricle 14 by the VAD 38. In many embodiments, the implanted coupler 12 and the inlet cannula 42 and/or the VAD 38 include suitable interfacing features to form a fluid tight seal between the coupler 12 and the inlet cannula 42 and/or the VAD 38 and secure attachment of the VAD 38 to the coupler 12. For example, the inlet cannula 42 can include one or more seal members (e.g., o-ring seals) that interface with both the inlet cannula 42 and the conduit 30 of the coupler 12 to form a fluid-tight seal between the inlet cannula 42 and the coupler 12. As another example, the pump assembly 40 can include one or more seal members that interface with both the pump assembly 40 and the coupler 12 to form a fluid-tight seal between the pump assembly 40 and the coupler 12. The inlet cannula 42 can have one or more features that interface with the coupler 12 and accommodate insertion of the inlet cannula 32 into the conduit 30 of the coupler 12 and prevent extraction of the inlet cannula 42 from the conduit 30 without the application of significant extraction force to the inlet cannula 42. For example, an external surface of the inlet cannula 42 can include a one-way locking catch and/or hook structure that that interfaces with the coupler 12 and accommodates insertion of the inlet cannula 42 into the conduit 30 and prevents extraction of the inlet cannula 42 from the conduit 30 without the application of significant extraction force to the inlet cannula 42. The pump assembly 40 and the inlet cannula 42 can also include one or more attachment features shaped to interface with complementarily-shaped attachment features included in the coupler 12 to secure attachment of the VAD 38 to the coupler 12.

Figure 9:
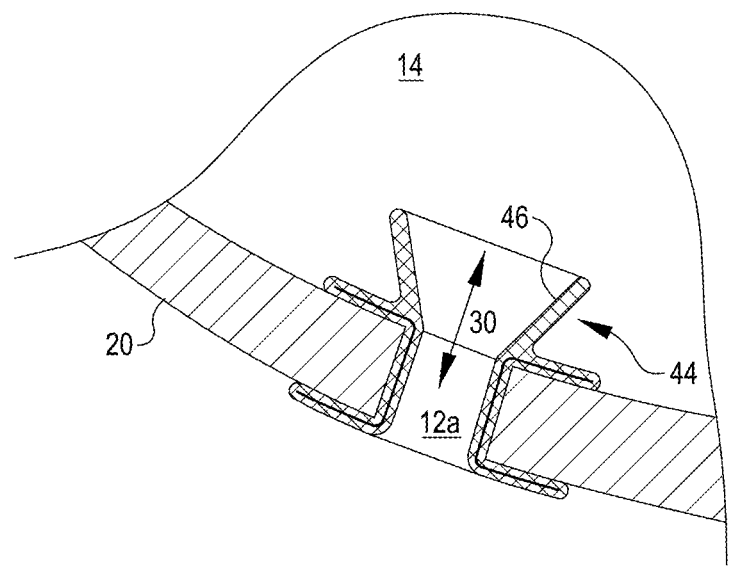
FIG. 9 shows an implanted coupler that includes an inlet portion that extends into the ventricle, in accordance with many embodiments.

FIG. 9 shows an embodiment of the coupler 12, referred to herein as coupler 12a, that includes an inlet portion 44 that extends into the ventricle 14. In the illustrated embodiment, the inlet portion 44 forms a portion of the conduit 30 having a tapering cross-sectional area, thereby providing a larger inlet area than a portion of the conduit 30 passing through the aperture in the myocardial wall 20, thereby providing improved flow characteristics in conjunction with a small puncture site that does not require coring, a suture ring, and all of the associated procedure time and complexity. The inlet portion 44 can include a suitable surface membrane 46 to inhibit thrombosis.

Figure 10:
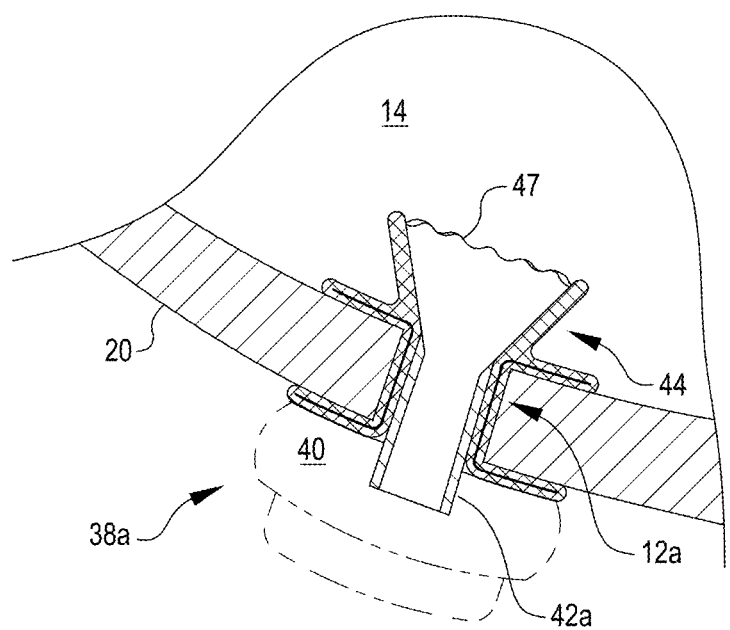
FIG. 10 shows an implanted coupler that includes an inlet portion that extends into the ventricle and has an inlet edge having one or more valleys between adjacent peaks, in accordance with many embodiments.

FIG. 10 shows a VAD 38a coupled with the implanted coupler 12a. In the illustrated embodiment, the VAD 38a includes a pump assembly 40 and an inlet cannula 42a, which extends from the pump assembly 40 and provides an inlet fluid channel by which blood flow is pumped from the ventricle 14 by the VAD 38a. The implanted coupler 12a and the inlet cannula 42a and/or the VAD 38a can include suitable interfacing features, such as the features described herein with respect to the VAD 38 and the coupler 12, to form a fluid tight seal between the coupler 12a and the inlet cannula 42a and/or the VAD 38a and secure attachment of the VAD 38a to the coupler 12a. In the embodiment illustrated in FIG. 10, the inlet portion 44 of the coupler 12a has an inlet edge 47 having one or more valleys between adjacent peaks. The one or more valleys are configured to maintain fluid communication between the ventricle 14 and pump assembly 40 if contact occurs between the inlet edge 47 and an inner surface of the ventricle 14.

Figure 11A:
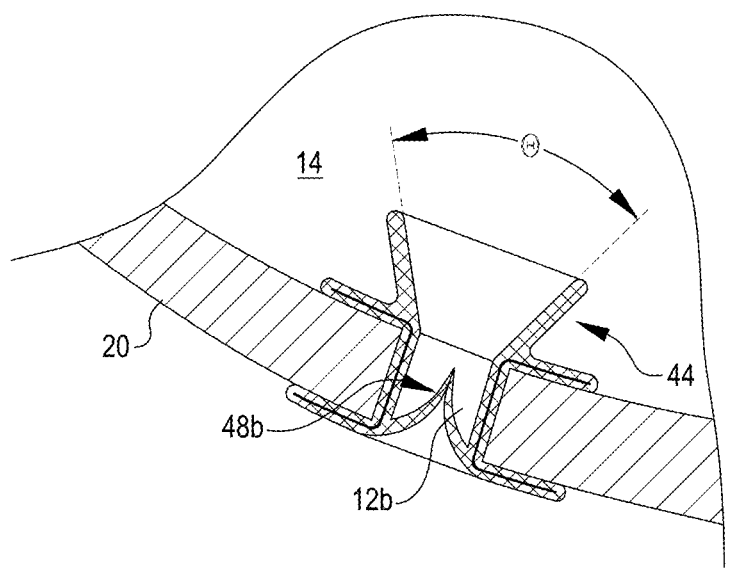
FIG. 11A shows an implanted coupler that includes a flow-blocking valve configured to block flow of blood from the ventricle prior to coupling of a VAD with the coupler, in accordance with many embodiments.
Figure 11B:
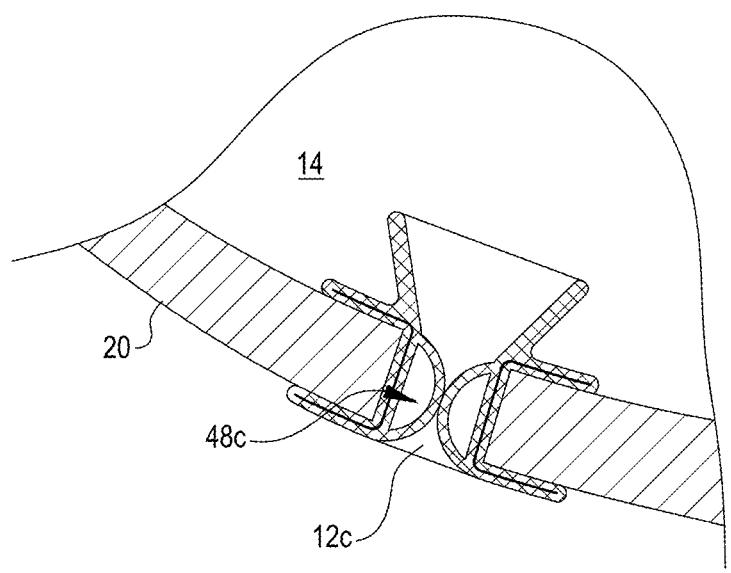
FIG. 11B shows another implanted coupler that includes a flow-blocking valve configured to block flow of blood from the ventricle prior to coupling of a VAD with the coupler, in accordance with many embodiments.
Figure 12:
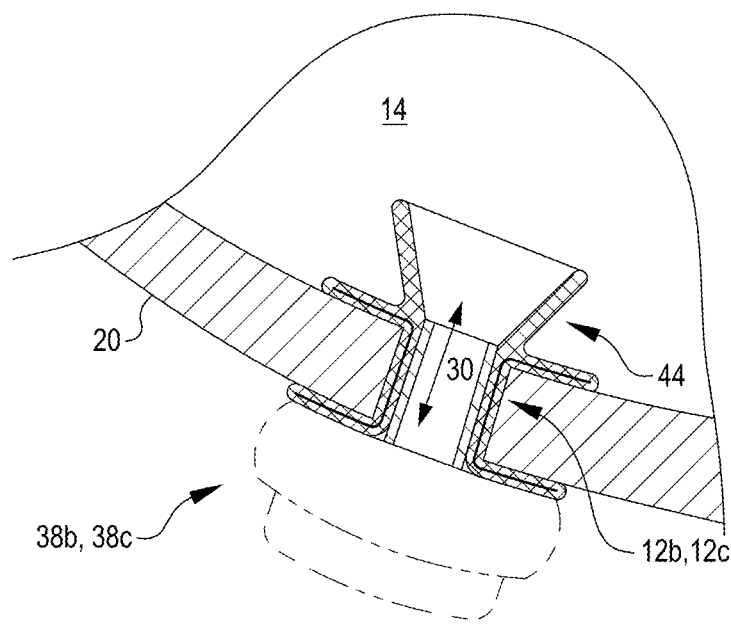
FIG. 12 shows the implanted coupler of FIG. 11A or FIG. 11B with a VAD coupled with the implanted coupler, in accordance with many embodiments.

FIG. 11A and FIG. 11B show embodiments of the coupler 12, referred to herein as coupler 12b, 12c, that includes a flow-blocking valve 48b, 48c. The flow-blocking valve 48b, 48c is shown in a flow-blocking configuration that blocks flow of blood from the ventricle 14 prior to coupling of a VAD 38 with the coupler 12b, 12c. The inlet portion 44 can also have any suitable angle θ or shape for receiving the flow of blood from the ventricle. Referring now to FIG. 12, the flow-blocking valve 48b, 48c is reconfigured from the flow-blocking configuration to the illustrated flow-accommodating configuration via insertion of an inlet cannula 42a into the conduit 30 of the coupler 12b, 12c, thereby interfacing with the flow-blocking valve 48b, 48c so as to hold the valve 48b, 48c open. It will be appreciated that the valve 48b, 48c may be positioned anywhere along a length of the access conduit, including outer or inner flanges.

Figure 13:
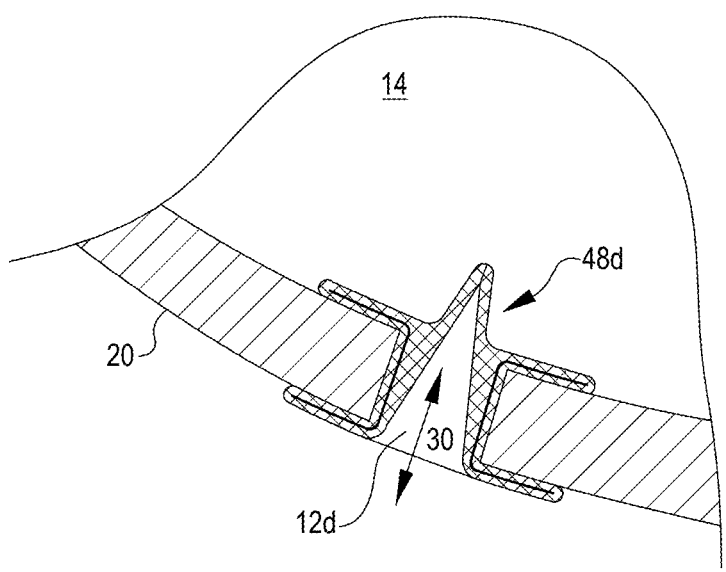
FIG. 13 shows another implanted coupler that includes a flow-blocking valve configured to block flow of blood from the ventricle prior to coupling of a VAD with the coupler, in accordance with many embodiments.
Figure 14:
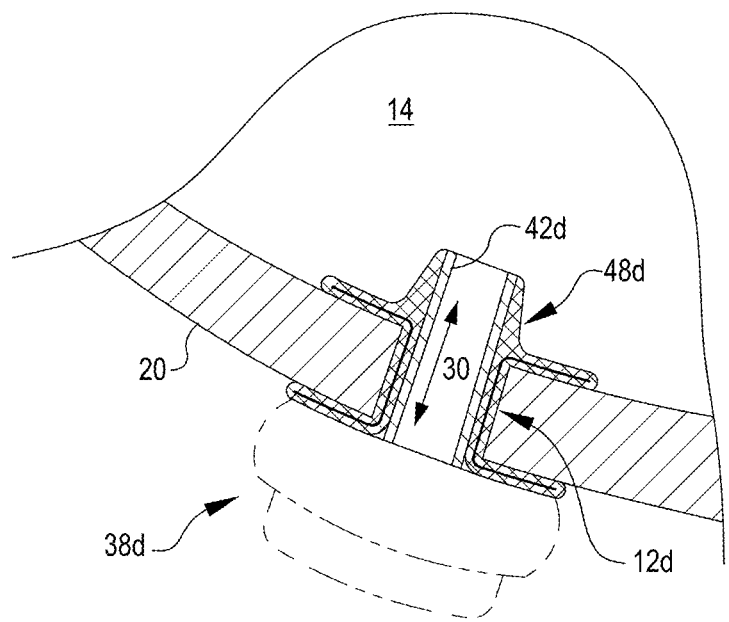
FIG. 14 shows the implanted coupler of FIG. 13 with a VAD coupled with the implanted coupler, in accordance with many embodiments.

FIG. 13 shows an embodiment of the coupler 12, referred to herein as coupler 12d, that includes a flow-blocking valve 48d. The flow-blocking valve 48d is shown in a flow-blocking configuration that blocks flow of blood from the ventricle 14 prior to coupling of a VAD 38d with the coupler 12d. The conduit 30 of the coupler 12d has a tapering cross-section throughout the depth of the coupler 12d so that insertion of an inlet cannula 42d into the conduit 30 results in increased radially-oriented interface pressure between the coupler 12d and the aperture in the heart wall 20 and reconfiguration of the valve 48d from the flow-blocking configuration to the flow-accommodating configuration. Referring now to FIG. 14, the flow-blocking valve 48d is reconfigured from the flow-blocking configuration to the illustrated flow-accommodating configuration via insertion of an inlet cannula 42d into the conduit 30 of the coupler 12d, thereby interfacing with the flow-blocking valve 48d so as to hold the valve 48c open.

Figure 15:
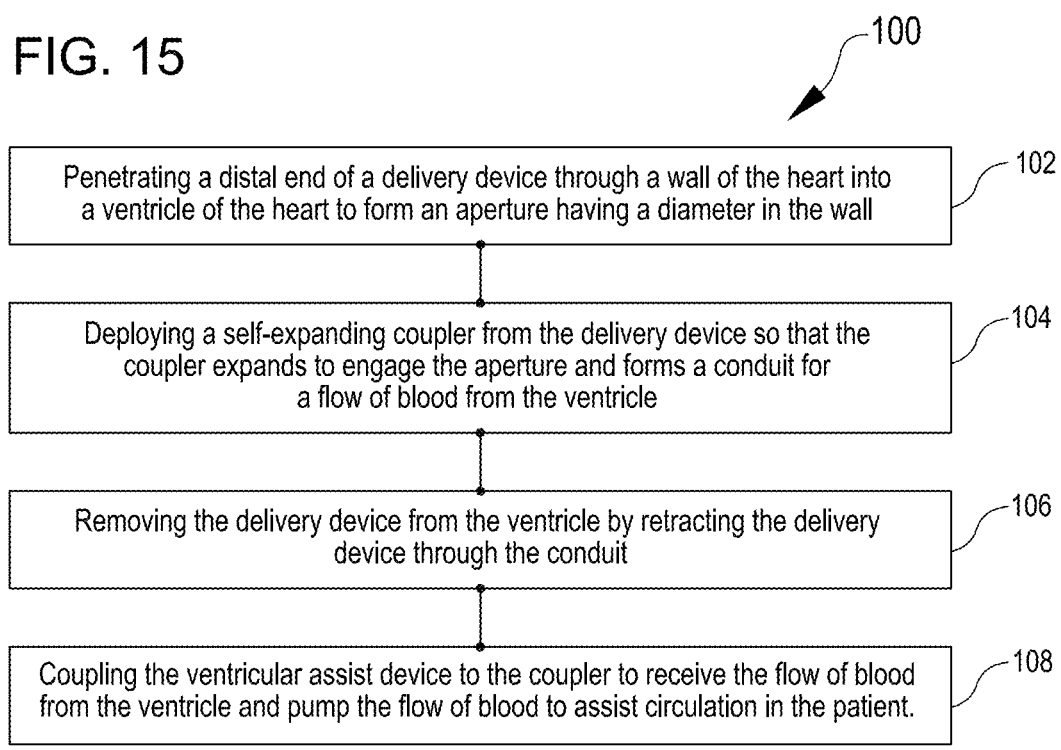
FIG. 15 shows a simplified block diagram of acts for a method for implanting a ventricular assist device in a patient, in accordance with many embodiments.

FIG. 15 shows a simplified block diagram of acts for a method 100 for implanting a VAD in a patient, in accordance with many embodiments. Any suitable coupler and delivery device for the coupler, including the couplers and delivery devices described herein, can be used to practice the method 100. The method 100 includes penetrating a distal end of a delivery device through a wall of a heart into a ventricle of the heart to form an aperture having a diameter in the wall (act 102).

The method 100 further includes deploying a self-expanding coupler from the delivery device so that the coupler expands to engage the aperture and forms a conduit for a flow of blood from the ventricle (act 104). Deploying the coupler from the delivery device can include reconfiguring the delivery device to release the coupler from a delivery configuration so that the coupler self-expands to a deployed configuration. Reconfiguring the delivery device to release the coupler from the delivery configuration can include retracting a sheath from a retention configuration in which the sheath retains the coupler in the delivery configuration to a release configuration in which the coupler is not retained by the sheath. Reconfiguring the delivery device to release the coupler from the delivery configuration can include retracting the sheath from the retention configuration to an inner flange release configuration in which the inner flange of the coupler protrudes radially from the delivery device and a portion of the coupler is retained by the sheath and deploying the coupler from the delivery device can include retracting the delivery device with the sheath in the inner flange release configuration to bring the inner flange into engagement with the inner surface of the wall of the heart. The method 100 can further include at least one of (a) engaging an inner surface of the wall of the heart with an inner flange of the coupler that protrudes radially relative to the aperture and (b) engaging an outer surface of the wall of the heart with an outer flange of the coupler that protrudes radially relative to the aperture. The method 100 can further include accommodating ingrowth of tissue from at least one of (a) the inner surface of the wall into the inner flange of the coupler, (b) the outer surface of the wall into the outer flange of the coupler, and (c) a surface of the aperture of the wall into a portion of the coupler engaged with the aperture.

The method 100 further includes removing the delivery device from the ventricle by retracting the delivery device through the conduit (act 106). To block flow of blood through the coupler following removal of the delivery device, the coupler can include a flow control portion reconfigurable from a flow blocking configuration to a flow accommodating configuration. Accordingly, the method 100 can further include blocking flow of blood through the conduit via the flow control portion in the flow blocking configuration prior to coupling the ventricular assist device to the coupler.

The method 100 further includes coupling the ventricular assist device to the coupler to receive the flow of blood from the ventricle and pump the flow of blood to assist circulation in the patient (act 108). Where the coupler includes a flow control portion, the method can include reconfiguring the flow control portion from the flow blocking configuration to the flow accommodating configuration to accommodate the flow of blood from the ventricle to the ventricular assist device for pumping to assist circulation in the patient. Reconfiguring the flow control portion from the flow blocking configuration to the flow accommodating configuration can include engaging an inlet conduit of the ventricular assist device with the flow control portion to reconfigure the flow control portion from the flow blocking configuration to the flow accommodating configuration.

In the following description, various embodiments of the present invention have been described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described. Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An implantable coupler for coupling a ventricular assist device with a ventricle of a heart of a patient, the implantable coupler comprising:
   a self-expandable frame configured to expand from a collapsed configuration sized to be enclosed within a sheath of a delivery device during insertion through an aperture in a wall of the ventricle to a deployed configuration in which the self-expandable frame (a) expands to engage the aperture, (b) expands the aperture, (c) forms a conduit for a flow of blood from the ventricle, (d) expands to form an inner flange that protrudes radially relative to the aperture and is configured to interface with an inner surface of the wall of the ventricle, (e) expands to form an outer flange that protrudes radially relative to the aperture and is configured to interface with an outer surface of the wall of the ventricle, and (f) expands to form an inlet flange that extends distally into the ventricle and away from the inner flange when in the deployed configuration, wherein the inlet flange defines an inlet portion of the conduit that has a larger cross-sectional area than a portion of the conduit passing through the aperture in the wall of the ventricle so as to improve flow characteristics; and
   a material layer supported by the self-expandable frame and accommodating ingrowth of tissue into the material layer from at least one of (a) the inner surface of the wall of the ventricle into a portion of the material layer disposed in the inner flange of the implantable coupler, (b) the outer surface of the wall of the ventricle into a portion of the material layer disposed in the outer flange of the implantable coupler, or (c) a surface of the aperture in the wall of the ventricle into a portion of the material layer disposed in a portion of the implantable coupler engaged with the aperture.

2. The implantable coupler of claim 1, wherein the implantable coupler includes a flow control portion reconfigurable from a flow blocking configuration that blocks flow of blood through the conduit prior to coupling of the ventricular assist device to the implantable coupler to a flow accommodating configuration that accommodates the flow of blood from the ventricle to the ventricular assist device for pumping to assist circulation in the patient.

3. The implantable coupler of claim 2, wherein the flow control portion is reconfigurable from the flow blocking configuration to the flow accommodating configuration via engagement of an inlet cannula of the ventricular assist device with the flow control portion to reconfigure the flow control portion.

4. The implantable coupler of claim 1, wherein the implantable coupler is configured for insertion of an inlet cannula of the ventricular assist device into the conduit of the implantable coupler so that a sealed attachment is formed between the inlet cannula and the implantable coupler.

5. The implantable coupler of claim 1, wherein the inlet flange the inlet portion of the conduit has a conical shape.

6. The implantable coupler of claim 5, wherein the inlet flange has an inlet edge shaped to form one or more valleys between consecutive and adjacent peaks, the one of more valleys being configured to maintain fluid communication between the ventricle and the conduit if contact occurs between the inlet edge and an inner surface of the ventricle.

7. The implantable coupler of claim 1, wherein the inlet portion of the conduit has a conical shape.

8. The implantable coupler of claim 1, wherein the self-expandable frame comprises a woven nickel titanium tube and the material layer comprises a polyester mesh.

9. The implantable coupler of claim 1, wherein the self-expandable frame is configured to engage an endothelial layer so as to create a blood contact surface that inhibits clotting and thrombus formation.

10. The implantable coupler of claim 1, wherein the inlet portion of the conduit is tapered to facilitate receiving blood from the ventricle.

11. The implantable coupler of claim 1, wherein the self-expandable frame further comprises a fibrotic mesh.

12. The implantable coupler of claim 11, wherein the fibrotic mesh is configured to induce endothelialization and stabilization of the implantable coupler relative to the wall of the ventricle.

13. The implantable coupler of claim 1, wherein the self-expandable frame comprises a braided fabric formed from a plurality of strands.

14. The implantable coupler of claim 1, wherein the outer flange is configured to self-expands to engage the outer surface of the wall of the ventricle when released from the sheath of the delivery device.

15. The implantable coupler of claim 1, wherein inlet flange comprises a surface membrane to inhibit thrombosis.

* * * * *